United States Patent
Zeller et al.

(10) Patent No.: US 12,216,189 B2
(45) Date of Patent: Feb. 4, 2025

(54) CREATING CALIBRATION DATA FOR PROCESSING RECORDED MEASUREMENT DATA OF AN OBJECT TO BE EXAMINED USING AN MR SYSTEM

(71) Applicant: Siemens Healthineers AG, Forchheim (DE)

(72) Inventors: Mario Zeller, Erlangen (DE); Adam Kettinger, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 322 days.

(21) Appl. No.: 17/950,653

(22) Filed: Sep. 22, 2022

(65) Prior Publication Data
US 2023/0093079 A1 Mar. 23, 2023

(30) Foreign Application Priority Data
Sep. 23, 2021 (DE) .................... 102021210655.2

(51) Int. Cl.
*G01R 33/58* (2006.01)
*A61B 5/00* (2006.01)
*A61B 5/055* (2006.01)
*G01R 33/563* (2006.01)

(52) U.S. Cl.
CPC .............. *G01R 33/58* (2013.01); *A61B 5/055* (2013.01); *A61B 5/4058* (2013.01); *A61B 5/7207* (2013.01); *G01R 33/56341* (2013.01); *A61B 2560/0223* (2013.01)

(58) Field of Classification Search
CPC .......... A61B 2560/0223; A61B 5/7207; A61B 5/055; A61B 5/4058; G01R 33/56341; G01R 33/58; G01R 33/5611
See application file for complete search history.

(56) References Cited

U.S. PATENT DOCUMENTS

2019/0041424 A1* 2/2019 Noda .................... G01P 15/18

OTHER PUBLICATIONS

Mozorov et al.:"Diffusion processes modeling in magnetic resonance imaging", Insights into Imaging (2020), pp. 1-9.
Setsompop, Kawin et al. "Blipped-Controlled Aliasing in Parallel Imaging for Simultaneous Multislice Echo Planar Imaging with Reduced g-Factor Penalty" Magnetic Resonance in Medicine, vol. 67, pp. 1210-1224, 2012 (first published online 2011) // DOI 10.1002/mrm.23097.

(Continued)

*Primary Examiner* — Gerald Johnson
(74) *Attorney, Agent, or Firm* — Banner & Witcoff Ltd.

(57) ABSTRACT

A method for creating calibration data for processing accelerated measurement data of an object to be examined using a magnetic resonance system. The method includes recording measurement data sets using an acquisition acceleration method, recording calibration data sets, and determining processed measurement data sets from the accelerated measurement data sets using the calibration data sets so that effects of the acquisition acceleration method used are eliminated in the processed measurement data sets. The recording of the calibration data sets includes an application of at least one attenuation method for attenuating signals causing phase errors.

14 Claims, 4 Drawing Sheets

(56) References Cited

OTHER PUBLICATIONS

Xie, B. Victor et al: "Robust EPI Nyquist Ghost Removal by Incorporating Phase Error Correction With Sensitivity Encoding (PEC-SENSE)"; Magnetic resonance in medicine; Year: 2018, vol. 79, No. 2, pp. 943-951.
Breuer, Felix A. et al. "Controlled Aliasing in Parallel Imaging Results in Higher Acceleration (CAIPIRINHA) for Multi-Slice Imaging" Magnetic Resonance in Medicine, vol. 53, No. 3, pp. 684-691, 2005 // DOI: 10.1002/mrm.20401.
Lyu, Mengye et al: "Robust SENSE reconstruction of simultaneous multislice EPI with low-rank enhanced coil sensitivity calibration and slice-dependent 20 Nyquist ghost correction"; Magnetic Resonance in Medicine; Year: 2018, vol. 80, No. 4, pp. 1376-1390.

\* cited by examiner

CREATING CALIBRATION DATA FOR PROCESSING RECORDED MEASUREMENT DATA OF AN OBJECT TO BE EXAMINED USING AN MR SYSTEM

TECHNICAL FIELD

The disclosure relates to a method for creating calibration data for completing undersampled recorded measurement data of an object to be examined using a magnetic resonance system.

BACKGROUND

Magnetic resonance technology (hereinafter the abbreviation MR stands for magnetic resonance) is a known technology with which images of the interior of an object to be examined can be created. In simple terms, the object to be examined is positioned in a magnetic resonance device in a comparatively strong, static, homogenous basic magnetic field, also referred to as a $B_0$ field, with field strengths of 0.2 Tesla to 7 Tesla and more, so that its nuclear spins are oriented along the basic magnetic field. In order to trigger nuclear magnetic resonance which can be measured as (echo) signals, radio-frequency excitation pulses (RF pulses) are irradiated into the object to be examined, the triggered nuclear magnetic resonance is measured as so-called k-space data and MR images are reconstructed on the basis thereof or spectroscopy data is determined. For spatial encoding of the measurement data, fast-switched magnetic gradient fields, called gradients for short, are superimposed on the basic magnetic field. A scheme used, which describes a time sequence of RF pulses to be irradiated and gradients to be switched, is referred to as a pulse sequence (scheme), or also as a sequence for short. The recorded measurement data is digitized and stored as complex numerical values in a k-space matrix. From the k-space matrix occupied by values, an associated MR image can be reconstructed, for example, using a multidimensional Fourier transformation.

Magnetic resonance imaging using a magnetic resonance system can serve to determine the presence and/or distribution of various tissues and/or a substance which is located in an object to be examined. The substance can be, for example, a potentially pathological tissue of the object to be examined, a contrast agent, a marker substance or a metabolic product.

Information about existing tissues and substances can be obtained in a variety of ways from the recorded measurement data. A relatively simple source of information is, for example, image data reconstructed from the measurement data. However, there are also more complex methods which, for example, determine information about the object to be examined from image data reconstructed from pixel time series of successively measured measurement data sets, i.e. measurement data sets which have been recorded by repetition of an acquisition scheme.

In principle, in order not to extend the repetition times TR in spite of higher resolution or also to accelerate the measurement in general, so-called parallel acquisition techniques (ppa: "partially parallel acquisition" or PAT: "Parallel Acquisition Technique") can be used, such as, for example, GRAPPA ("GeneRalized Autocalibrating Partially Parallel Acquisition") or SENSE ("Sensitivity Encoding"), in which only an amount of measurement data which is undersampled according to the Nyquist theorem in the k-space is recorded with the aid of a plurality of RF coils. The "missing" measurement data is supplemented in these methods on the basis of sensitivity data of the RF coils used and calibration data from the measured measurement data before the image data is reconstructed. Due to the fact that only some of the measurement data actually required for complete scanning is recorded (typically, for example, only half (=acceleration factor R=2) or a quarter (=acceleration factor R=4), or even only an eighth (=acceleration factor R=8) or less), the readout time required for reading the measurement data is reduced and thus the repetition time is reduced. However, the sensitivity data of the RF coils and calibration data mentioned are required, requiring additional measurements.

The desire for ever faster MR images in the clinical environment, on the other hand, leads to a renaissance of methods in which a plurality of images is recorded simultaneously. In general, these methods can be characterized in that, at least during a part of the measurement, transverse magnetization of at least two layers is used simultaneously for the imaging process (multi-layer imaging, layer multiplexing, Simultaneous Multi-Slice (SMS)). In contrast, in the case of established "multi-layer imaging", the signal of at least two layers is recorded alternately, in other words, completely independently of one another with a correspondingly longer measurement time.

Known SMS methods are, for example, methods which use methods from the aforementioned imaging by means of ppa, in which knowledge about the sensitivity distribution of the receiver coils used in the acquisition of the measurement data is used as additional information in order to replenish measurement data undersampled in accordance with Nyquist, in the direction of layer selection, in order to separate signals received from a plurality of layers in a superimposed manner into signals of the individual layers. These methods also include, for example, the CAIPIRINHA technique, as described by Breuer et al. in "Controlled Aliasing in Parallel Imaging Results in Higher Acceleration (CAIPIRINHA) for Multi-Slice Imaging", Magnetic Resonance in Medicine 53, 2005, p. 684-691, and the blipped CAIPIRINHA technique, as described by Setsompop et al. in "Blipped-Controlled Aliasing in Parallel Imaging for Simultaneous Multislice Echo Planar Imaging With Reduced g-Factor Penalty", Magnetic Resonance in Medicine 67, 2012, p. 1210-1224, wherein the g-factor mentioned in the latter title ("g-factor", short for "geometry factor") is a measure of the separability of the various receiver coils used.

A magnetic resonance image can be composed of a multiplicity of individual partial measurements in which raw data from various layers of the object to be examined is recorded in order to subsequently reconstruct volume image data therefrom.

In the case of methods which determine information about the object to be examined from measurement data sets recorded through repeated measurement (a series of measurements) using an acquisition scheme, a specific measurement parameter of the acquisition scheme can be varied in order, for example, to analyze the effect of this measurement parameter on the object to be examined and finally to be able to draw diagnostic conclusions from the result. In this case, a measurement parameter is expediently varied in such a way that the contrast of a specific material type excited during the measurements, for example of a tissue type of the object to be examined or of a chemical substance which is significant for most or certain tissue types, such as, for example, water, is influenced as strongly as possible by the variation of the measurement parameter. This ensures that the effect of the measurement parameter on the object to be examined is particularly clearly visible.

A typical example of such series of measurements with variation of a measurement parameter strongly influencing the contrast are so-called diffusion-weighted imaging (DWI)) methods. Diffusion is understood to mean the Brownian motion of molecules in a medium. In diffusion imaging, a plurality of images with different diffusion directions and weightings are generally recorded and combined with one another. The strength of the diffusion weighting is usually defined by the so-called "b-value". The diffusion images with different Diffusion directions and weightings or the images combined therefrom can then be used for diagnostic purposes. Thus, using suitable combinations of the recorded diffusion-weighted images, parameter maps with particular diagnostic significance can be created, such as, for example, maps which reproduce the Apparent Diffusion Coefficient (ADC) or Fractional Anisotropy (FA).

In diffusion-weighted imaging, additional gradients reflecting the diffusion direction and weighting are introduced into a pulse sequence in order to visualize or measure the diffusion properties of the tissue. These gradients lead to tissues with rapid diffusion (e.g. cerebrospinal fluid, CSF) being subject to a stronger signal loss than tissues with slow diffusion (e.g. the gray matter in the brain). The resulting diffusion contrast is becoming increasingly important clinically and applications now go far beyond the classic early detection of ischemic stroke.

Diffusion imaging is often based on echo planar imaging (EPI) due to the short acquisition time of the EPI sequence per image and its robustness to motion.

In the context of an EPI measurement, it may be possible for the recorded measurement data to have artifacts which impair the imaging of the object to be examined. In detail, in the context of reading out the measurement data using EPI, a gradient train is typically applied which comprises a plurality of gradients of different polarity in a sequential sequence. Depending on the polarity, the gradient echoes created by the gradient train are sometimes referred to as even or odd. On account of the alternating polarity of the gradients of the gradient train, measurement data for different lines of the k-space are measured in the alternating direction. This means, for example, that measurement data for a first line are measured from left to right and for a second line which is arranged in the k-space adjacent to the first line, from right to left.

In the case of EPI measurements, errors of the phase (phase errors) can occur, which cause artifacts. For example, displacements of the phase of the measurement data for rows in k-space with different measuring directions can occur, as described above. This can occur, for example, due to time inaccuracies when applying the gradient pulses and/or during digitization in the context of recording the measurement data and/or due to eddy current effects. Furthermore, for example, movements of the object to be examined, including pulsating movements which influence the spins which generate the signals to be recorded, can cause phase errors which also make their correction more difficult. Such an N/2 ghost artifact can occur in the MR image as a "ghost" image of the object to be examined and typically have a lower intensity than the actual image of the object to be examined and furthermore be displaced in a positive and/or negative direction with respect to the actual image of the object to be examined.

Methods for correcting such N/2 ghost artifacts are already known. However, these are not satisfactorily effective when using parallel acquisition techniques, such as GRAPPA, in particular in neuronal MR imaging.

SUMMARY

An object of the disclosure is to improve the quality of measurement data recorded using parallel acquisition techniques despite possible phase errors occurring.

The disclosure is based on the finding that phase errors contained in recorded calibration data lead to discrepancies between calibration data and measurement data recorded using an acceleration method and to be processed with the calibration data, which discrepancies have a negative effect on the result of the processing.

A method according to the disclosure for creating calibration data for processing accelerated measurement data of an object to be examined using a magnetic resonance system comprises the steps:

Recording of measurement data sets using an acquisition acceleration process,
Recording of calibration data,
Determination of processed measurement data sets from the accelerated measurement data sets using the calibration data sets, so that effects of the acquisition acceleration method used are eliminated in the processed measurement data sets,
wherein the recording of the calibration data sets comprises the use of at least one attenuation method for attenuating signals causing phase errors.

By using at least one attenuation method for attenuating signals causing phase errors in the recording of calibration data sets, the calibration data sets obtained are not subject to the undesired phase errors. Thus, measurement data sets processed using the calibration data sets are not negatively affected by the phase errors thus avoided in the calibration data sets. As a result, artifacts in the measurement data and image data reconstructed therefrom are reduced and the image quality is improved.

For example, movements, in particular pulsating movements of spins in the object to be examined, can lead to phase errors in the recording of calibration data sets, which lead to a discrepancy between the recorded calibration data sets and recorded measurement data sets to be processed with the calibration data sets.

Signals of spins in a cerebrospinal fluid (CSF) are subject, for example, to a pulsating movement on the living patient as an object to be examined, leading to a pulsating phase and thus to phase errors. If such a signal with phase errors, such as, for example, a signal of spins from a cerebrospinal fluid, is attenuated by the method according to the disclosure when recording calibration data sets, a discrepancy between calibration data and measurement data to be processed with the calibration data sets can be reduced or even avoided.

A magnetic resonance system according to the disclosure comprises a magnet unit, a gradient unit, a radio-frequency unit and a control facility designed to carry out a method according to the disclosure with an attenuation unit.

A computer program according to the disclosure implements a method according to the disclosure on a control facility when it is executed on the control facility.

The computer program can also be in the form of a computer program product which can be loaded directly into a memory of a control facility, with program code means, in order to carry out a method according to the disclosure when the computer program product is executed in the computing unit of the computer system.

An electronically readable data carrier according to the disclosure comprises electronically readable control information stored thereon which comprises at least one computer program according to the disclosure and is designed in such a way that when the data carrier is used in a control facility of a magnetic resonance system, it carries out a method according to the disclosure.

The advantages and aspects specified in relation to the method also apply analogously to the magnetic resonance system, the computer program product and the electronically readable data carrier.

DESCRIPTION OF THE DRAWINGS

Further advantages and details of the present disclosure will emerge from the exemplary aspects described hereinafter and with reference to the diagrams. The examples given do not constitute a limitation of the disclosure. The diagrams show.

DETAILED DESCRIPTION

Figure 1:
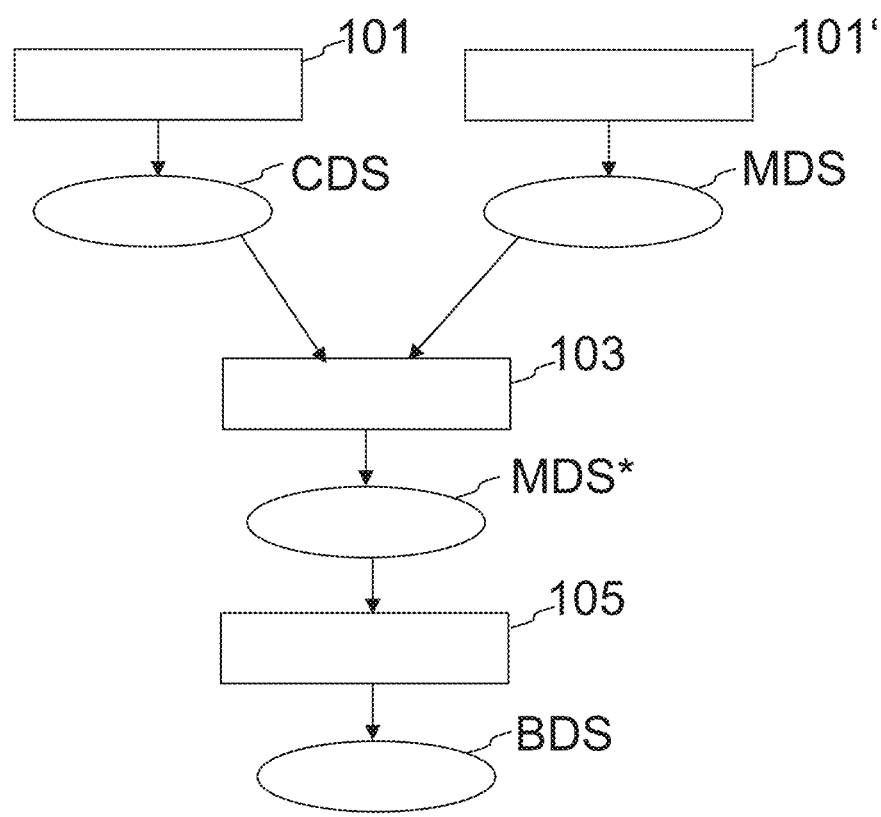
FIG. 1 is a diagrammatic flow chart of a method according to the disclosure for creating calibration data for processing accelerated measurement data of an object to be examined using a magnetic resonance system.

FIG. 1 is a diagrammatic flow chart of a method according to the disclosure for creating calibration data for processing accelerated measurement data of an object to be examined.

Measurement data sets MDS are recorded using an acquisition acceleration process (block 101').

In this case, a measurement data set MDS is a set of measurement data which is recorded in a recording, for example, after an RF excitation pulse.

Possible acquisition acceleration methods are, for example, parallel acquisition techniques, in particular GRAPPA, with which the measurement data sets MDS are recorded undersampled in accordance with an acceleration factor R.

Additionally or alternatively, possible acquisition acceleration methods are layer multiplexing methods, in particular a CAIPIRINHA technique, with which the measurement data sets MDS from at least two layers are recorded in a superimposed manner.

The measurement data sets MDS can be recorded in the context of a diffusion imaging method. As described above, various measurement data sets MDS with different diffusion weights are to be recorded.

Figure 2A:
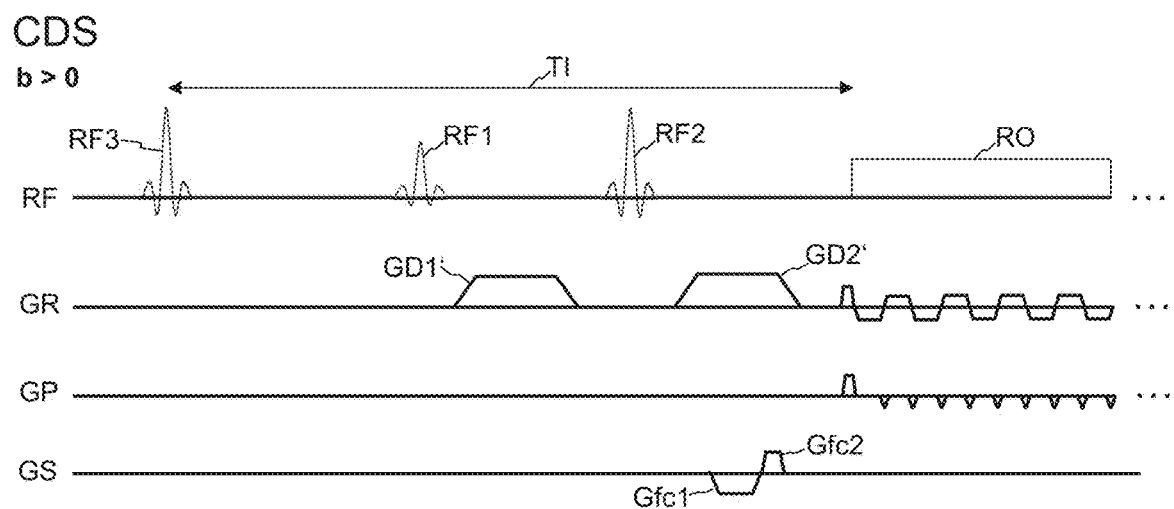
FIGS. 2A-2C are diagrammatic views of parts of pulse sequence schemes for acquiring diffusion-weighted and non-diffusion-weighted measurement data sets and calibration data sets as can be used, for example, according to the disclosure.
Figure 2B:
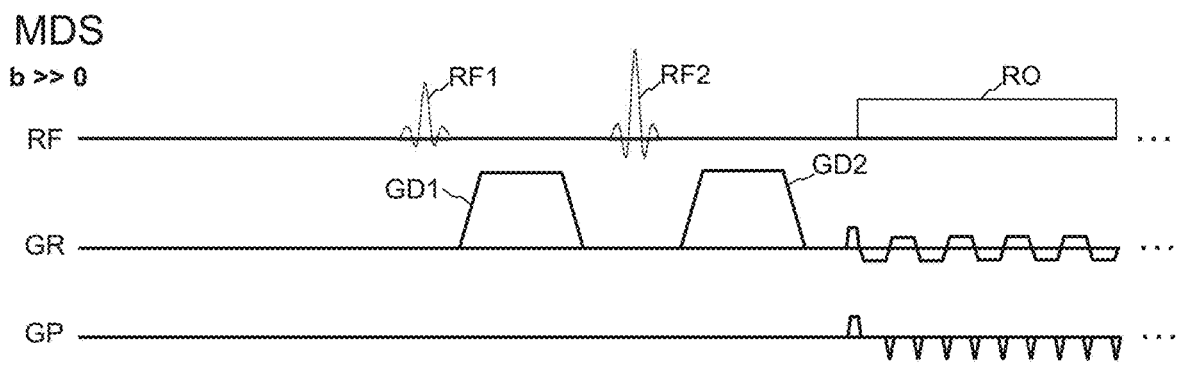
Figure 2C:
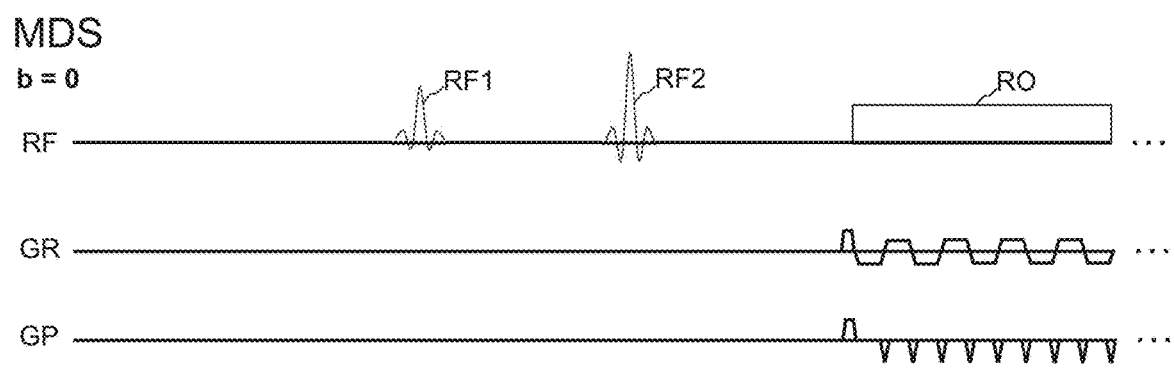

FIGS. 2B and 2C show diagrammatic views of exemplary parts of pulse sequence schemes for detecting diffusion-weighted (b>>0) and associated non-diffusion-weighted (b=0) measurement data sets MDS.

In the example shown, in each case an RF excitation pulse RF1 and an RF refocusing pulse RF2 following the RF excitation pulse RF1 are irradiated, and the echo signals produced are recorded as measurement data in a readout period RO. During the recording of the measurement data in the readout period RO, the examples show gradients switched in the readout direction GR and in the phase encoding direction GP, as are used in EPI techniques for recording measurement data.

Figure 4:
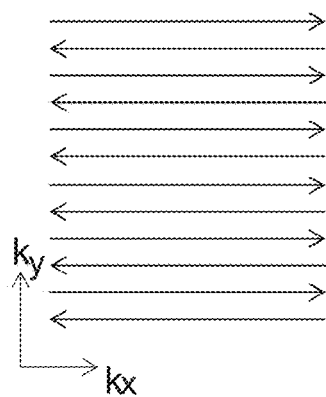
FIG. 4 is a diagrammatic view of a possible acquisition scheme of recorded undersampled measurement data sets and calibration data sets.
Figure 4:
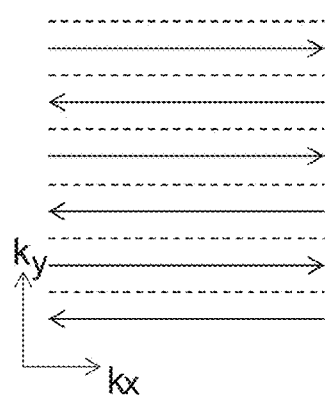

A diagrammatic view of an example of a possible associated EPI acquisition scheme of recorded undersampled measurement data sets MDS is shown in FIG. 4 (on the right). In the example shown, the k-space lines (here: every second line) shown in dashed lines in the readout direction $k_x$ are not recorded, as a result of which the measurement data set MDS (with an acceleration factor R=2) is undersampled in the phase encoding direction $k_y$. K-space lines for which measurement data are recorded are shown as arrows which, in accordance with the polarity of the gradients switched during the readout period RO, alternately point "from right to left" and "from left to right" in the readout direction GR, in order to clarify the readout direction.

For diffusion weighting, diffusion gradients GD1, GD2 (here, for example, in readout direction GR) are switched as shown in FIG. 2B in the pulse sequence scheme for detecting a diffusion-weighted measurement data set MDS (b>>0). In the example, the diffusion gradients GD1, GD2 shown have a large amplitude and are thus selected here in such a way that a high b-value (b>>0), in particular the highest, of the b-values to be used in the context of the desired diffusion imaging, e.g. b=1000, is achieved. A pulse sequence scheme for detecting an associated non-diffusion-weighted measurement data set MDS (b=0) does not comprise any diffusion gradients.

Calibration data sets CDS are recorded (block 101), the recording of the calibration data sets CDS comprising the use of at least one attenuation method for attenuating undesired signals with phase errors in the recorded calibration data sets CDS. In this case, a calibration data set CDS is a set of calibration data which is required for the desired processing of a measurement data set MDS.

The attenuation method attenuates, for example, signals of spins in the object to be examined, in which phase errors are caused by a movement, in particular a pulsating movement, in the object to be examined. Ideally, the attenuation method attenuates the undesired signals until complete suppression of these. In this way, a negative effect of phase errors otherwise contained in the calibration data during processing of measurement data sets MDS using the calibration data sets CDS can be avoided or at least reduced.

In particular, the attenuation method can attenuate signals of spins in a cerebrospinal fluid (CSF). Especially cerebrospinal fluid is often subject to pulsation according to the heartbeat of the object to be examined, which leads to corresponding pulsation of the phases of signals of the spins of a cerebrospinal fluid recorded using magnetic resonance technology.

The attenuation method may comprise switching diffusion gradients. For this purpose, during the recording of the calibration data sets CDS, diffusion gradients are switched in a manner analogous to that in the case of a diffusion-weighted measurement data set MDS.

Diffusion gradients lead to an attenuation of signals from spins in diffusing media. If the signals to be attenuated are signals from diffusing media, an attenuation according to the disclosure can thus be achieved by switching diffusion gradients.

For example, the media water or cerebrospinal fluid have similar diffusivity. Signals from spins present in these media can be attenuated by diffusion gradients.

In FIG. 2A, an exemplary diagrammatic part of a pulse sequence scheme for detecting calibration data sets CDS is compared with parts of pulse sequence schemes for detecting diffusion-weighted measurement data sets MDS (b>>0) (shown in FIG. 2B) and non-diffusion-weighted measurement data sets MDS (b=0) (shown in FIG. 2C) already described above in the text.

Analogously to the recording of the measurement data sets MDS shown, in the example shown in FIGS. 2A-2C, an RF excitation pulse RF1 and an RF refocusing pulse RF2 following the RF excitation pulse RF1 are also radiated during the recording of a calibration data set CDS, and the resulting echo signals are recorded as measurement data in a readout period RO. Again, the example shows gradients switched in the readout direction GR and in the phase encoding direction GP during the recording of the measurement data in the readout period RO as are used in EPI techniques for recording measurement data.

An example of a possible associated EPI acquisition scheme of recorded calibration data sets CDS is shown diagrammatically in FIG. 4 (on the left). In the example shown, all the k-space lines shown in the readout direction $k_x$ are recorded. The calibration data set CDS is thus complete (according to Nyquist). The arrows representing the recorded k-space lines again point alternately "from right to left" and "from left to right" in the readout direction GR, in accordance with the polarity of the gradients switched during the readout period RO, in order to clarify the readout direction during the recording. The distance in the phase encoding direction $k_y$ of the recorded k-space lines, which is smaller for the calibration data set CDS in comparison with the measurement data set MDS, corresponds to the acceleration factor R, and in the associated pulse sequence schemes of FIGS. 2A-2C can be determined at the correspondingly lower amplitudes of the gradients (gradient blips) in the phase encoding direction GP, which are switched during a readout period RO, during the recording of the calibration data set CDS in comparison with the amplitudes of the switched gradients (gradient blips) in the phase encoding direction GP, which are switched during a readout period RO, during the recoding of the measurement data sets MDS.

For diffusion weighting, as shown in FIG. 2B in the pulse sequence scheme for detecting a diffusion-weighted measurement data set MDS (b>>0), diffusion gradients GD1', GD2' (here, for example, in readout direction GR) can be switched.

When recording calibration data sets CDS, switched diffusion gradients GD1, GD2' can be selected in such a way that they do not exceed a maximum strength, i.e. that their amplitude does not exceed a maximum value. In this way, the gradient unit with which the gradients are generated can be protected and other possible undesired side effects of switched gradients, such as eddy currents, for example, can be reduced. In the article by Morozov et al. "Diffusion processes modeling in magnetic resonance imaging", Insights Imaging, p. 60 (2020) it is shown that diffusion gradients which correspond to small to medium b-values (approximately b=100 to b=500), can be sufficient to attenuate signals from spins, e.g. from cerebrospinal fluid.

The attenuation method can, additionally or alternatively to diffusion gradients GD1', GD2', comprise an inversion method which comprises irradiating an inversion pulse RF3, RF3a, RF3b, RF3c for an inversion time TI before recording RO of the calibration data sets CDS in a readout period RO. Inversion methods for suppressing or attenuating signals in magnetic resonance technology are known in principle.

In the part of a pulse sequence scheme for acquiring calibration data sets CDS shown in FIG. 2A, a possible inversion pulse RF3 is shown, which is irradiated for an inversion time TI before recording the calibration data set CDS in the readout period RO. The inversion pulse RF3 and, in particular, the inversion time TI are selected here in such a way that signals to be attenuated are attenuated to a desired extent. A customary inversion time of signals from spins from cerebrospinal fluid is, for example, approximately 2.5 seconds.

If an inversion method and a switching of diffusion gradients GD1', GD2' are combined in the attenuation method, the inversion time TI to be selected can be reduced as, after the reduced inversion time TI, remaining signals to be attenuated are further attenuated by the switched diffusion gradients GD1', GD2'. Additionally or alternatively, with such a combination, the strength of the switched diffusion gradients GD1', GD2' can also be reduced as the signals to be attenuated are already attenuated by the inversion method.

Calibration data sets CDS can be recorded interleaved for various subvolumes to be measured, for example layers, of an overall desired target volume of the object to be examined. Such an interleaved recording of calibration data sets for different subvolumes reduces the duration of the total time required for the recording of all calibration data sets CDS.

In particular, if the attenuation method comprises an inversion method which extends the overall recording time for a calibration data set CDS by the inversion time TI to be awaited between the inversion pulse RF3 and the beginning of the readout period RO, a significant reduction in the duration required overall for the recording of all desired calibration data sets CDS for different subvolumes can be achieved by such an interleaved recording of calibration data sets CDS. In this case, it can be achieved that the duration which is required overall for recording all desired calibration data sets CDS is extended only by an inversion time TI, in spite of the attenuation method used, compared to a duration which is required overall for recording all the desired calibration data sets CDS without attenuation methods. This is usually the case, for example, if the durations for the individual recordings of all desired calibration data sets CDS taken together do not exceed the inversion time TI.

Figure 3:
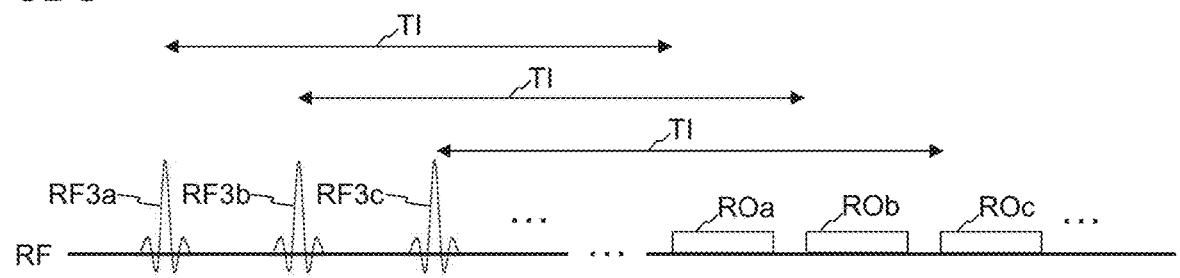
FIG. 3 is a diagrammatic view of an excerpt from a pulse sequence scheme for acquiring calibration data sets for clarifying a possible variant when recording calibration data sets according to the disclosure.

FIG. 3 shows a diagrammatic view of an excerpt of a pulse sequence scheme for detecting calibration data sets CDS for clarifying this possible variant of the interleaved recording of calibration data sets CDS for various subvolumes.

In the example shown in FIG. 3, a plurality of, for example three, inversion pulses RF3a, RF3b, RF3c are irradiated in chronological order into the object to be examined, each of the irradiated inversion pulses RF3a, RF3b, RF3c acting in each case only on a defined subvolume a, b, c, for example different layers a, b, c to be measured, of the object to be examined. Calibration data sets CDS for the respective subvolumes a, b, c, are recorded in each case after the same inversion time TI after irradiation of the associated inversion pulse RF3a, RF3b, RF3c in an associated readout period ROa, ROb, ROc. The calibration data can be generated and read out in a customary and known manner, for example also as in FIGS. 2A-2C.

The attenuation method can additionally or alternatively comprise switching of flow compensation gradients. By means of flow compensation, phase errors in recorded calibration data caused by a movement, for example a flowing or pulsating movement, in the object to be examined can be suppressed. For suppression of phase errors caused by a pulsating movement, the duration of a readout period RO for a calibration data set should be as short as possible with respect to the frequency of the pulsation in order to achieve the desired attenuation. The flow compensation gradients can be designed in a conventional manner.

The switched flow compensation gradients can be switched at least in the direction of a direction of movement of the spins causing the signals to be attenuated, in order to avoid at least a major part of undesired phase errors in this (main) direction of movement. For example, for a pulsating movement of cerebrospinal fluid, it can be assumed that in a patient as an object to be examined, it runs in a "head-foot" direction, and thus typically in the direction of slice selection.

In the part of a pulse sequence scheme for acquiring calibration data sets CDS shown in FIG. 2A, possible flow compensation gradients Gfc1, Gfc2 with different polarity are shown, which are switched here after the RF refocusing pulse RF2 and before the readout period RO in the direction of slice selection GS. Further gradients possibly to be switched in the direction of slice selection GS, for example for a slice selection, are known per se and therefore not shown (as in the examples of recordings of measurement data sets MDS).

It is also conceivable to switch flow compensation gradients between the RF excitation pulse RF1 and the RF refocusing pulse RF2 and/or in the phase encoding direction GP and/or readout direction GR.

Processed measurement data sets MDS* are determined from the accelerated recorded measurement data sets MDS using the calibration data sets CDS (block 103), so that effects of the acquisition acceleration method used are eliminated in the processed measurement data sets MDS*.

If a parallel acquisition technique was used as the acquisition acceleration method, the processing of the measurement data sets MDS recorded in an undersampled manner comprises completing the measurement data sets MDS recorded in an undersampled manner to form processed measurement data sets MDS*. The effect of the incompleteness of the recorded measurement data sets MDS caused by the parallel acquisition technique as a result of the undersampling is eliminated by completion using the calibration data sets CDS.

If a layer multiplexing method was used as the acquisition acceleration method, the processing of the superimposed recorded measurement data sets MDS comprises separating the superimposed recorded measurement data sets MDS into processed (single layer) measurement data sets MDS* assigned in each case only to a single layer. The effect, caused by the layer multiplexing method, of the superimposition of the measurement data sets MDS recorded simultaneously and thus collapsed for a plurality of layers is eliminated by the separation using the calibration data sets CDS in single-layer measurement data sets MDS* of individual layers measured simultaneously.

Image data sets BDS can be reconstructed from the processed measurement data sets MDS* (block 105).

The image data sets reconstructed in this way from measurement data sets processed with calibration data sets recorded using at least one attenuation method according to the disclosure have an enhanced image quality compared to image data sets reconstructed from measurement data sets processed from calibration data sets recorded in a conventional manner and contain fewer artifacts.

Figure 5:
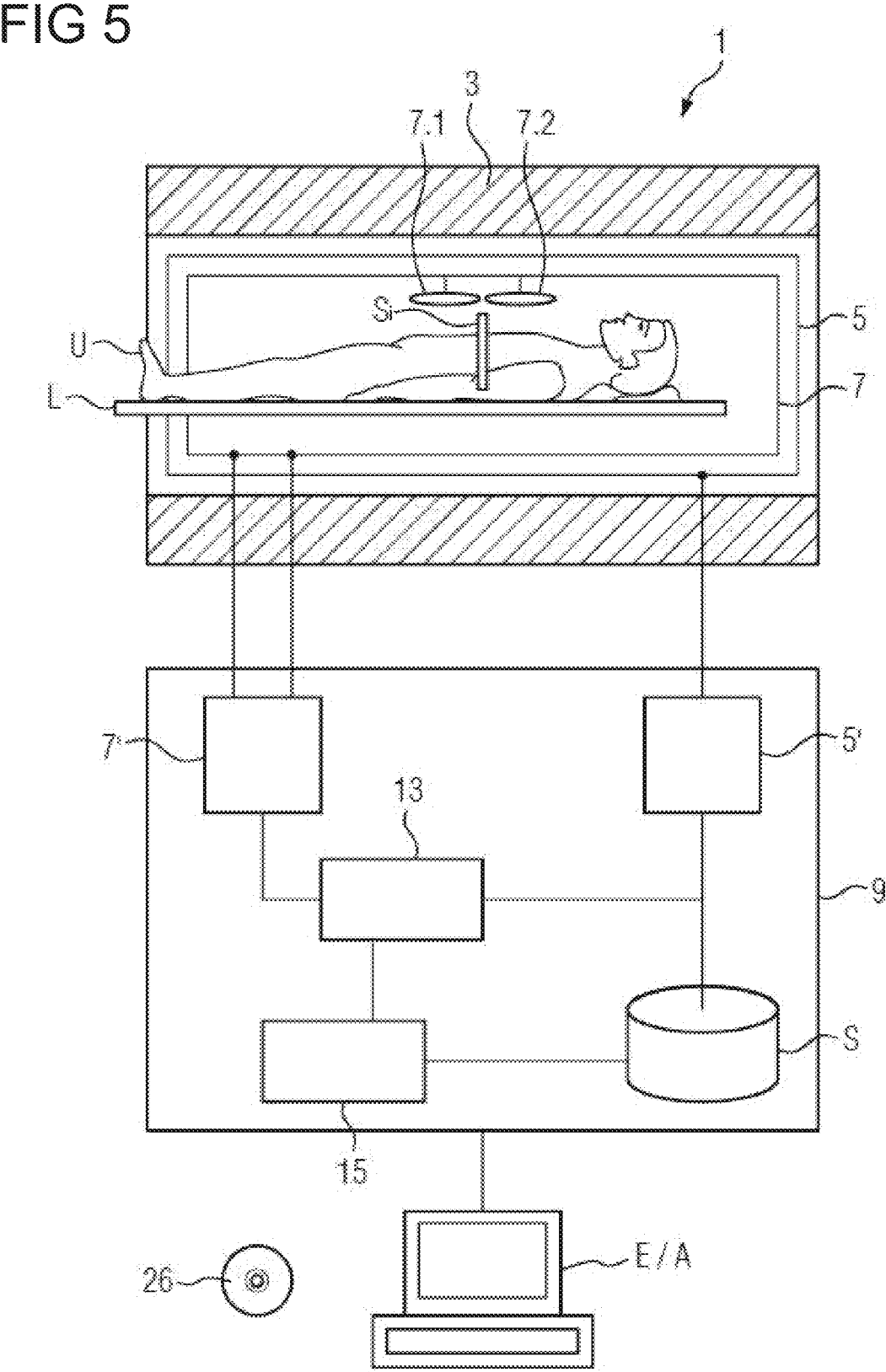
FIG. 5 is a diagrammatic view of a magnetic resonance system according to the disclosure.

FIG. 5 shows a diagrammatic view of a magnetic resonance system 1 according to the disclosure. This comprises a magnet unit 3 for generating the basic magnetic field, a gradient unit 5 for generating the gradient fields, a radio-frequency unit 7 for irradiation and for receiving radio-frequency signals and a control facility 9 designed to carry out a method according to the disclosure.

FIG. 5 provides only a rough diagrammatic view of these partial units of the magnetic resonance system 1. In particular, the radio-frequency unit 7 may consist of a plurality of subunits, for example of a plurality of coils such as the coils 7.1 and 7.2 shown in a diagrammatic view or more coils which may be designed either only for transmitting radio-frequency signals or only for receiving the triggered radio-frequency signals or for both.

For the examination of an object to be examined U, for example a patient or also a phantom, this can be introduced into the measurement volume of the magnetic resonance system 1 on a bed L. The layer or the slab Si represents an exemplary target volume or, in the case of using a layer-multiplexing method, a part of a target volume consisting of different layers of the object to be examined from which echo signals are to be recorded and included as measurement data.

The control facility 9 serves to control the magnetic resonance system 1 and can in particular control the gradient unit 5 using a gradient controller 5' and the radio-frequency unit 7 using a radio-frequency transceiver controller 7'. The radio-frequency unit 7 may comprise a plurality of channels on which signals can be transmitted or received.

The radio-frequency unit 7, together with its radio-frequency transceiver controller 7', is responsible for generating and irradiating (transmitting) a radio-frequency alternating field for manipulating the spins in a region to be manipulated (for example, in layers S to be measured) of the object to be examined U. In this case, the center frequency of the radio-frequency alternating field, also referred to as the B1 field, is generally set as far as possible in such a way that it is close to the resonance frequency of the spins to be manipulated. Deviations from the center frequency by the resonance frequency are referred to as off-resonance. In order to generate the B1 field, controlled currents are applied to the RF coils in the radio-frequency unit 7 using the radio-frequency transceiver controller 7'.

Furthermore, the control facility 9 comprises an attenuation unit 15 with which attenuation according to the disclosure of undesired signals, which lead to phase errors, can be generated. The control facility 9 as a whole is designed to carry out a method according to the disclosure.

A computing unit 13 comprised by the control facility 9 is designed to perform all the computing operations necessary for the necessary measurements and determinations. Intermediate results and results required for this or determined in the process can be stored in a storage unit S of the control facility 9. The units shown here are not necessarily to be understood as physically separate units, but merely represent a subdivision into sense units which, however, can also be realized for example, in fewer or even in only one physical unit.

Via an input/output facility I/O of the magnetic resonance system 1, for example, control commands can be sent by a user to the magnetic resonance system and/or results of the control facility 9, such as for example, image data, can be displayed.

A method described herein can also be in the form of a computer program product which comprises a program and implements the method described on a control facility 9 when it is executed on the control facility 9. Likewise, an electronically readable data carrier 26 with electronically readable control information stored thereon can be present, which comprises at least one such computer program product as described and is designed in such a way that it carries out the method described when the data carrier 26 is used in a control facility 9 of a magnetic resonance system 1.

The invention claimed is:

1. A method for creating calibration data for processing accelerated measurement data of an object to be examined using a magnetic resonance system, the method comprising:
    recording measurement data sets using an acquisition acceleration method;
    recording calibration data sets; and
    determining processed measurement data sets from the accelerated measurement data sets using the calibration data sets, so that effects of the acquisition acceleration method used are eliminated in the processed measurement data sets,
    wherein the recording of the calibration data sets comprises an application of at least one attenuation method for attenuating signals affected by phase errors.

2. The method as claimed in claim 1, wherein the at least one attenuation method comprises attenuating signals of spins in the object to be examined, which cause phase errors in the object to be examined due to a pulsating movement.

3. The method as claimed in claim 1, wherein the attenuation method comprises attenuating signals of spins in a cerebrospinal fluid.

4. The method as claimed in claim 1, wherein the measurement data sets are recorded in a context of a diffusion imaging method.

5. The method as claimed in claim 1, wherein the attenuation method comprises switching of diffusion gradients.

6. The method as claimed in claim 5, wherein the switched diffusion gradients do not exceed a maximum strength.

7. The method as claimed in claim 1, wherein the attenuation method comprises an inversion method which comprises irradiating an inversion pulse for an inversion time before recording of the calibration data sets.

8. The method as claimed in claim 1, wherein the calibration data sets for different subvolumes of the examination object to be measured are recorded in a nested manner.

9. The method as claimed in claim 1, wherein the attenuation method comprises switching of flow compensation gradients.

10. The method as claimed in claim 9, wherein the flow compensation gradients are switched at least in the direction of a direction of movement of spins causing the signals to be attenuated.

11. The method as claimed in claim 1, wherein the acquisition acceleration method is a GeneRalized Autocalibrating Partially Parallel Acquisition (GRAPPA) technique with which the measurement data sets are undersampled according to an acceleration factor, and the processing of the undersampled measurement data sets comprises completing the undersampled measurement data sets to form complete measurement data sets.

12. The method as claimed in claim 1, wherein the acquisition acceleration method is a Controlled Aliasing in Parallel Imaging Results in Higher Acceleration (CAIPIRINHA) technique with which the measurement data sets are recorded in a superimposed manner from at least two layers, and the processing of the measurement data sets recorded in the superimposed manner comprises a separation of the measurement data sets recorded in the superimposed manner into single-layer measurement data sets.

13. A magnetic resonance system, comprising:
    a magnet unit;
    a gradient unit;
    a radio-frequency unit; and
    a control facility having a radio-frequency transceiver controller and an attenuation unit, wherein the control facility is designed to carry out a method as claimed in claim 1 on the magnetic resonance system.

14. An non-transitory electronically readable data carrier with electronically readable control information stored thereon, which comprises a computer program such that when the data carrier is used in a control facility of a magnetic resonance system, the computer programs carries out the method as claimed in claim 1.

* * * * *